United States Patent [19]

Futschik et al.

[11] Patent Number: 5,635,397
[45] Date of Patent: Jun. 3, 1997

[54] THERMAL CHAMBER FOR TEMPERATURE CONTROL OF BIOLOGICAL SPECIMENS

[75] Inventors: Karl Futschik, Maria Enzersdorf; Roland Schiessl, Vienna; Helmut Pfützner, Bad Gastein; Gert Fränzl, Purkersdorf, all of Austria

[73] Assignee: Sy-Lab Vertriebsgesellscaft m.b.H., Purkersdorf, Austria

[21] Appl. No.: 292,828

[22] Filed: Aug. 19, 1994

[30] Foreign Application Priority Data

Aug. 20, 1993 [AT] Austria .................................. 1684/93

[51] Int. Cl.$^6$ .................................................. C12M 3/00
[52] U.S. Cl. ........................ 435/286.1; 435/288.7; 435/303.1; 62/3.6; 62/457.9; 237/3; 237/14; 165/48.1
[58] Field of Search ........................... 435/286.1, 292.1, 435/303.1, 288.7; 62/3.6, 440, 457.1, 457.9; 237/3, 14; 165/48.1, 61, 63

[56] References Cited

U.S. PATENT DOCUMENTS

| 4,701,415 | 10/1987 | Dutton et al. | 435/289 |
| 5,149,654 | 9/1992 | Gross et al. | 435/303.1 |
| 5,404,935 | 4/1995 | Lieberman | 165/48.1 |

FOREIGN PATENT DOCUMENTS 8705623  9/1987  WIPO .

*Primary Examiner*—David A. Redding
*Attorney, Agent, or Firm*—Herbert Dubno

[57] ABSTRACT

A thermal chamber, e.g. for culturing bacteria, has between a pair of sidewalls, a plurality of replaceable bridge members or plates which can be formed with undulating broad surfaces or grooves to accommodate flasks so that gaps between the plates receive measuring devices for turbidity or the like. The plates are thermally conductive and abut the walls which can be provided with heating or cooling units.

19 Claims, 1 Drawing Sheet

THERMAL CHAMBER FOR TEMPERATURE CONTROL OF BIOLOGICAL SPECIMENS

FIELD OF THE INVENTION

The present invention relates to a thermal chamber having at least one thermally conductive wall for the control of the temperature, e.g. the heating, cooling or maintaining of a constant temperature, of a plurality of biological samples in measuring vessels, especially for monitoring the growth of microorganisms, e.g. bacteria.

BACKGROUND OF THE INVENTION

In order to provide a stable environment for the growth of bacteria in measuring vessels, such as flasks or test tubes or cultivation tubes, either thermal chambers or thermoblocks are generally employed. Thermal chambers generally have areas all around the samples or vessels or at least over a substantial portion of the peripheries thereof which are not obstructed to allow viewing of the interiors of the vessels and, in addition to observation, analysis of the contents of the vessels. Thermoblocks, by contrast, have compartments closely receiving the vessels with the walls of the compartments practically hugging the walls of the vessels to maximize thermal conductivity between the block and each vessel. While the latter ensures an effective thermal equilibrium between the block and the interior of the vessel, it has the drawback that the vessel walls are not accessible for manipulation or measurement, the ability to observe the contents of the vessel is restricted and the system has a very high mass.

Measurements of bacterial growth can be effected electrically via the impedance measurement of the contents of the vessel between two or more electrodes. Alternatively, the cloudiness or degree of turbidity can be determined and radiation, utilizing the visible light spectrum or invisible waves, can be utilized. It is also possible to employ electrical or magnetic fields or radioactive media to monitor the bacterial culture. The display or registering of the parameters of bacterial cultures can be effected automatically during a particular observation period and the culturing process can be programmed or controlled automatically.

Notwithstanding the fact that prior art thermal chambers and thermoblocks have been found to be highly effective in achieving temperature equilibration among the samples and between the samples and the heating and cooling units of the apparatus, in practically all of the earlier devices the compromises between accessibility to the sample vessel and the need for close proximity of the sample vessel to a wall of the thermally modulated structure have led to unacceptable results.

OBJECTS OF THE INVENTION

It is, therefore, the principal object of the present invention to provide an improved thermal chamber which ensures internally a highly uniform temperature distribution but which nevertheless allows optical monitoring and even radiation detection of the culturing process and the bacterial growth.

It is another object of this invention to provide an improved thermal chamber which has the advantages of earlier systems including some of the advantages of a thermoblock but which is free from the drawbacks outlined above.

Still another object of this invention is to provide an improved thermal chamber for the purposes described which is of comparatively light weight, low cost and high efficiency.

SUMMARY OF THE INVENTION

These objects are attained in accordance with the invention by providing the interior of a thermal chamber having a pair of walls at least one of which is thermally conductive, with thermally conductive bridge members or plates in heat-conducting relationship with the walls for homogenizing the temperature distribution and wherein these bridge pieces have a spacing at least in specific regions which is equal to or greater than a dimension of the cross section of the vessel.

More particularly, a thermal chamber for the cultivation of bacteria samples in respective vessels can comprise:

a pair of spaced-apart juxtaposed walls, at least one of the walls being thermally conductive;

means for regulating a temperature of the one of the walls; and at least two mutually spaced thermally conductive bridging members spanning between the walls and in thermally conductive contact with the one of the walls, the bridging members receiving the vessels between them in thermally conductive contact with the vessels for homogeneously distributing heat among the vessels, the bridging members being spaced apart by distances at least equal to a width of the vessels at least at regions along the bridging members receiving the vessels.

The bridge members or plates, which are independent bodies capable of insertion or removal between the thermally conductive walls, function as heat conductors in heat conducting relationship with the heated or cooled thermally conductive walls of the chamber and extend into the interior in which they conductively heat the vessels in contact with these bridge members and/or radiantly heat or cool the latter.

Laterally a thermal transfer is effected by a preferably large-area intimate contact of the bridge member or plate with the thermally conductive wall or both thermally conductive walls.

A multiplicity of such bridge members or plates can be provided in the chamber and can serve as partitions between rows off the measuring vessels. This ensures a thermal decoupling of vessels from one another while nevertheless guaranteeing a thermal homogenization through the intermediary of the thermally conductive bridge members or plates. The effect on neighboring vessels of a replacement of the vessel or a manipulation thereof can be minimized.

The bridge members or plates, apart from other thermally conductive and heat distribution function can also have a retaining function for the measurement vessels when they are in line or surface contact with the latter.

It has been found to be advantageous to provide a multiplicity of plates forming the bridge members, especially of aluminum, so that the plates are generally parallel to one another and extend between and transversely to a pair of thermally conductive walls provided with the heating and cooling means.

The plates can be formed with right angle bends at one or both of their ends so that these bent legs or shanks can lie with significant contact areas against the heated or cooled walls of the thermal chamber and ensure heat flow from or to these walls.

According to a feature of the invention, the broad surfaces of the plates are of an undulating configuration, i.e. correspond to a sinusoidal pattern as defined by generatrices moved along a sinusoidal line in the pattern of corrugated surfaces. The sinusoidal patterns on opposite sides of each plate or of juxtaposed plates may be of the same phase or may be phase shifted by 180°. The outer configuration of the plates can correspond to corrugated plates although the plates will be substantially thicker, for example, of a thickness of 8 millimeters. The plates can also vary in thickness periodically say between 20 mm and 8 mm to provide the undulating patterns. With the sidewalls juxtaposed channel like recess can be provided to accommodate the plates.

The plates thus form thermally conductive inserts in the thermal chamber, between which the measuring vessels are retained.

For a surface contact between the plates and the usual circularly cylindrical measuring vessels, at least the concavity of these undulating surface of a plate can approximate a circular arc curvature. This ensures that the recesses of the undulations in which the vessel can be received can better accommodate the vessel.

The plates can also be provided with mutually juxtaposed parallel channel shaped recesses in an otherwise planar surface, the recess being of semicircular or V-shaped cross section for engaging the vessels between them. The parallel surfaces of the plates define a gap and the recesses can be provided in pairs, mirror symmetrically opposite one another.

Corrugations may provide spacing of the plates while the grooves or cutouts form regions engaging the vessels.

It has been found to be especially advantageous for the plates to be received in respective frames, e.g. via rails, which allow the plates to slide into the frames and position the plates relative to one another. The frames can form parts of the thermally conductive walls or can be thermally conductive and connected to these walls e.g. via rails to promote heat transfer with minimal losses. A rail insertion system of this type allows quick replacement of the plates by others of different cross section, wall thickness or shape. The frames may hold electrical conductors or terminals for individual heating and cooling devices in the plates operating, for example, in accordance with the Peltier effect. This is especially advantageous with large thermal chambers, where replacement of the vessels is frequent, or where different temperature conditions are to be maintained at different zones within the thermal chamber.

Means can be provided to enable cooling or heating air to be blown into the gaps between the ridge members or plates.

In the spaces between the bridge members or plates, optical measuring devices can be provided, e.g. sensors for turbidity measurements in transmitted light or reflection processes, the sensors being provided so that they can be inserted or removed form the gaps. Other devices which can be inserted are those which are used for illumination, irradiation, or application of magnetic or electrical fields.

For example, printed circuit boards can be inserted into the gaps with electrical components, light-conductor systems can be provided in the gaps with optical fibers or the like and the gaps can be utilized to receive tubes for aerating the samples or for monitoring evolved gases. Indeed mechanical components can also be inserted into the gap to effect, for example, vibration or agitation of the vessels.

Magnetic components can be inserted to excite magnetic stirrers or particles in the vessels. All of these techniques can be used to accelerate microorganism growth or promote other advantageous results.

Since an impedance measurement between electrodes in the vessel may have significance under different environmental conditions, it is advantageous to provide electrodes for such impedance measurement and to provide radiation sources, for example light sources in the gap for comparative measurements. These light sources can be switched on and off.

BRIEF DESCRIPTION OF THE DRAWING

The above and other objects, features, and advantages will become more readily apparent from the following description, reference being made to the accompanying drawing in which.

SPECIFIC DESCRIPTION

Figures 1, 2, 3:
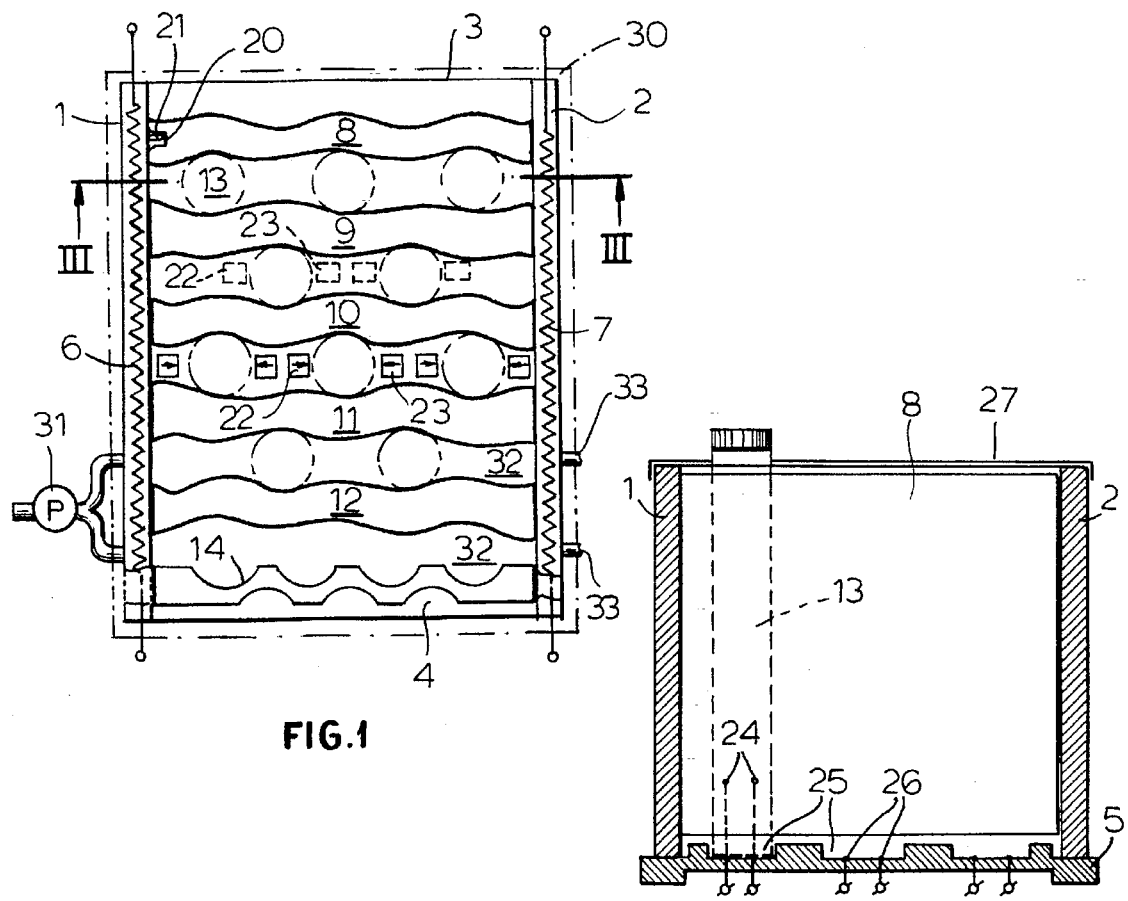
FIG. 1 is a plan view in highly diagrammatic form illustrating a part of a thermal chamber in accordance with the invention.
FIG. 2 is a view similar to FIG. 1 illustrating various modifications thereof.
FIG. 3 is a section taken along the line III—III of FIG. 1.

As can be seen from FIGS. 1 and 3, a thermal chamber, e.g. for the culturing of bacteria in measuring vessels such as cylindrical tubes composed of glass, can comprise four sidewalls 1, 2, 3, 4 disposed in pairs 1, 2 and 3, 4, respectively with the sidewalls of the pairs mutually parallel and spaced apart. A bottom plate 5 is provided.

Two of the sidewalls 1, 2 are provided with heating or cooling coils or mats 6, 7 and the heating and cooling can be effected via fluid traversing the coils, electric resistance heating or Peltier effect devices. Linde-process heating or cooling can also be used.

Thermal insulation as represented by the dot-dash lines 30 can surround the thermal chamber on all sides.

From FIG. 1 it is also apparent that the thermal chamber can be of any optional length.

In the interior of the thermal chamber, thermally conductive bridge members in the form of plates 8, 9, 10, 11, 12 are provided which interconnect the walls 1 and 2 and are parallel to each other and to the walls 3 and 4. At their ends, the plates 8 through 12 are in thermally conducting relationship with the walls 1 and 2.

To keep the thermal transfer losses between the walls 1 and 2 and the plates 8 through 12 as low as possible, contact surfaces or transitions between the plates are relatively large and a tight fit is provided between the individual plates and the walls 1 and 2. In one preferred construction, the sidewalls 1, 2 are held against the ends of the plates 8 through 12 by tension screws.

The broad sides of the plates 8 through 12 are corrugated or substantially sinusoidal as may correspond to undulations generated by straight line generatrices parallel to one another and moved along a sinusoidal line on opposite sides of each plate.

The undulations of each plate on opposite sides are here of the same phase while the undulations of juxtaposed plates are counterphase, i.e. offset in phase by 180° so that concavities of two opposite plates lie opposite one another and each pair of concavities can receive a respective cylindrical culturing vessel 13.

In the embodiment shown in FIG. 1, the plates 8 through 12 have relatively flat corrugations. The corrugations can be deeper and between the plates and the vessels, surface contact can be provided over angles of 90° if desired. The plates can be composed of aluminum machined to form the corrugations or cast from an aluminum alloy.

In FIG. 1 an additional bridge-forming plate 14 is shown which has planar broad faces with channel shaped recesses of circular cylindrical shape to receive the culture flasks. Such a plate can be easily fabricated.

FIG. 2 shows at A, B and C further variants of plates 15, 16, 17 and 18 which can be received in heat conducting relationship between the two thermally conducted sidewalls 1 and 2.

The plate 15 has corrugated broad surfaces with the corrugations on opposite sides in counterphase, i.e. phase shifted by 180°. When such plates are used in the thermal chamber, the culture flasks 13 lie in orthogonal rows and are not offset from one another from row to row as has been shown in FIG. 1.

The plate 16 has V-section grooves forming seats for the culture vessels 13 and these grooves are in line with one anther on opposite sides of each plate.

The plates 17 and 18 have their ends abutting the sidewalls 1 and 2 formed as angles so that broad legs or shanks 19 abut the sidewalls and promote heat transfer between the plaates and the sidewalls. The legs 19 can contact adjacent plates and form spacers defining the gaps between the plates in which the vessels are accommodated. The walls 1 and 2 can be stressed against the plates.

In FIG. 1, for positioning the plates, each plate is formed with aa groove at its end as represented at 20 and in which aa rail 21 can be received. The rails 21, preferably of U-shape, can engage the plates 8 through 12 or 15 and 16 laterally and from the bottom.

Between each pair of plates 8 through 12, 15 16 there is formed a gap or space enabling access to the measuring vessels 13 from the side and therefore, illumination or irradiation and optical measurement. In FIGS. 1 and 3 sensors 22 and 23 are provided for such measurement.

The plates serve for thermal conductivitity in the interior off the thermal chamber and ensure homogeneous temperature distribution as well as discreet environmental zones so that a decoupling of the environment of culture flasks 13 from one another is ensured. Additional heating or cooling in the plates enables local effects to be established and can eliminate influence of an effect by one another, e.g. by the removal of a flask. Further measurements can be carried out electrically, e.g. by impedance measurement between two electrodes 24 built into a flask ring and engaging contacts 26 in recesses 25 which are formed in the bottom plate 5 and center the flasks 13. The flasks 13 stand in the recesses 25.

The thermal chamber can be covered from above by a cover 27.

The thermal chamber can be of modular construction and can be increased in size by replacement of the plates to accommodate flasks of various sizes and for measurements in the gap between the plates, printed circuit boards can be inserted which can include elements for illumination or irradiation on one side of the flask and light measurement on the opposite side of the flask. Such means are represented at 22 and 23. Reference characters 22 and 23 can also represent any other measuring devices including optical fibers or light conductors. Variation of thermal characters of the chamber can be readily accommodated with the device described and because of the modular construction, storage of the component on manufacture is simplified. As can be seen in FIG. 1 as well, means, for example, the blower 31 can be provided on one side of each gap 32 while outlets 33 are provided on the opposite side to allow heated or cooled air to be blown through the gaps.

We claim:

1. A thermal chamber for controlling temperature of a plurality of biological samples in respective measurement vessels, said thermal chamber comprising:
    a pair of spaced-apart juxtaposed walls, at least one of said walls being thermally conductive;
    means for regulating a temperature of said one of said walls; and
    at least two removable and replaceable mutually spaced thermally conductive bridging members in the form of solid metal plates spanning between said walls and in thermally conductive contact with said one of said walls over a contact area along an end thereof, said bridging members receiving said vessels between them in thermally conductive contact with said vessels whereby each of said vessels is in contact with two of said bridging members for homogeneously distributing heat among said vessels, said bridging members being spaced apart by distances at least equal to a width of said vessels at least at regions along said bridging members receiving said vessels.

2. The thermal chamber defined in claim 1 wherein said means for regulating includes a heater.

3. The thermal chamber defined in claim 1 wherein a multiplicity of said plates are provided between said pair of thermally conductive walls and in thermally conductive contact therewith, said vessels being each receivable between a pair of said plates.

4. The thermal chamber defined in claim 3 wherein said plates are composed of aluminum.

5. The thermal chamber defined in claim 3 wherein said plates have broad sides with generally sinusoidal undulations defined by generatrices following sinusoidal lines.

6. The thermal chamber defined in claim 5 wherein the sinusoidal undulations on opposite broad sides of each plate are of the same phase.

7. The thermal chamber defined in claim 5 wherein the sinusoidal undulations on opposite broad sides of each plate are shifted in phase by 180°.

8. The thermal chamber defined in claim 5 wherein the sinusoidal undulations of the juxtaposed broad sides of each pair of plates are shifted in phase by 180°.

9. The thermal chamber defined in claim 5 wherein concave parts of the sinusoidal undulations at least approximate circular arcs.

10. The thermal chamber defined in claim 3 wherein said plates have parallel broad surfaces formed with opposing mirror-symmetrical grooves receiving each of said vessels.

11. The thermal chamber defined in claim 10 wherein said grooves are of V cross section.

12. The thermal chamber defined in claim 3 wherein said plates are slidable into frames with rails to position said plates along said wall.

13. The thermal chamber defined in claim 12 wherein said frames are provided with electrical connections to respective heating or cooling elements in and individual to said plates.

14. The thermal chamber defined in claim 3, further comprising means for blowing heated or cooled air into spaces between said plates.

15. The thermal chamber defined in claim 3, further comprising electrical, optical magnetic or mechanical measuring means including sensors for turbidity measurement in light transmission or reflective processes, or illumination or irradiation or by application of a magnetic or electric field in spaces between said plates to monitor microorganism growth in said vessels.

16. The thermal chamber defined in claim 3 wherein below said vessels a bottom plate is provided with terminals connectable with probes in said vessels for impedance measurements therein, a light source being provided between said plates and adapted to be turned on and off for comparative measurements.

17. A thermal chamber for controlling temperature of a plurality of biological samples in respective measurement vessels, said thermal chamber comprising:
    a pair of spaced-apart juxtaposed walls, at least one of said walls being thermally conductive;

means for regulating a temperature of said one of said walls; and at least two mutually spaced thermally conductive bridging members spanning between said walls and in thermally conductive contact with said one of said walls, said bridging members receiving said vessels between them in thermally conductive contact with said vessels for homogeneously distributing heat among said vessels, said bridging members being spaced apart by distances at least equal to a width of said vessels at least at regions along said bridging members receiving said vessels, said means for regulating including a cooler.

18. The thermal chamber defined in claim 1 wherein said walls are mutually parallel.

19. A thermal chamber for controlling temperature of a plurality of biological samples in respective measurement vessels, said thermal chamber comprising:

a pair of spaced-apart juxtaposed walls, at least one of said walls being thermally conductive;

means for regulating a temperature of said one of said walls; and at least two mutually spaced thermally conductive bridging members spanning between said walls and in thermally conductive contact with said one of said walls, said bridging members receiving said vessels between them in thermally conductive contact with said vessels for homogeneously distributing heat among said vessels, said bridging members being spaced apart by distances at least equal to a width of said vessels at least at regions along said bridging members receiving said vessels, both of said walls being provided with said means for regulating.

* * * * *